(12) United States Patent
Suga et al.

(10) Patent No.: US 8,994,802 B2
(45) Date of Patent: Mar. 31, 2015

(54) ENDOSCOPE

(71) Applicant: Olympus Medical Systems Corp., Tokyo (JP)

(72) Inventors: Takeshi Suga, Tokyo (JP); Hiroshi Tsuyuki, Tokyo (JP); Mitsujiro Konno, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/156,913

(22) Filed: Jan. 16, 2014

(65) Prior Publication Data

US 2014/0198194 A1    Jul. 17, 2014

Related U.S. Application Data

(63) Continuation of application No. PCT/JP2013/070316, filed on Jul. 26, 2013.

(30) Foreign Application Priority Data

Aug. 30, 2012    (JP) ................................ 2012-190436

(51) Int. Cl.
*H04N 7/18*    (2006.01)
*G02B 23/24*    (2006.01)
(Continued)

(52) U.S. Cl.
CPC .............. *G02B 23/243* (2013.01); *G02B 21/36* (2013.01); *G02B 23/24* (2013.01); *G02B 23/26* (2013.01);
(Continued)

(58) Field of Classification Search
CPC .. A61B 1/00096; A61B 1/00188; A61B 1/05; G02B 21/36; G02B 23/24; G02B 23/243; G02B 23/26; H04N 7/183

USPC ........ 348/65, 71, 72, 76, 68, 61, 45; 600/109, 600/118, 181, 117
See application file for complete search history.

(56) References Cited

U.S. PATENT DOCUMENTS 6,241,656 B1 * 6/2001 Suga .............................. 600/109
2001/0031912 A1 10/2001 Adler
(Continued)

FOREIGN PATENT DOCUMENTS

| | | |
|---|---|---|
| JP | 11-197097 | 7/1999 |
| JP | 11-197098 | 7/1999 |

(Continued)

OTHER PUBLICATIONS

International Search Report, dated Nov. 5, 2013, issued in corresponding International Application No. PCT/JP2013/070316.

*Primary Examiner* — Behrooz Senfi
(74) *Attorney, Agent, or Firm* — Kenyon & Kenyon LLP (57) ABSTRACT

An endoscope includes an objective optical system at a distal end of an inserted portion to acquire a subject image; a part that splits the subject image into two optical images focused differently; an imaging device that acquires two images by simultaneously capturing the optical images arranged on an imaging surface; and a part for cutting out at least abutting portions of the optical images on the imaging device, wherein A+B>C+D, where A is half the maximum length of light-receiving regions for the optical images at the imaging surface; where TW is an entry angle at the imaging surface when A is at the maximum image height and d is an optical-path-length difference between the optical images, B=d×tan TW; C is half the length of the light-receiving regions in a direction of the optical images arranged on the imaging surface; and D is a distance between the two light-receiving regions.

7 Claims, 5 Drawing Sheets

(51) Int. Cl.
*G02B 21/36* (2006.01)
*G02B 23/26* (2006.01)
*A61B 1/00* (2006.01)
*H04N 13/00* (2006.01)
*A61B 1/05* (2006.01)

(52) U.S. Cl.
CPC ......... *A61B 1/00096* (2013.01); *A61B 1/00188* (2013.01); *H04N 7/183* (2013.01); *A61B 1/05* (2013.01)
USPC .............................. 348/65; 348/45; 600/109

(56) References Cited

U.S. PATENT DOCUMENTS

| | | | |
|---|---|---|---|
| 2004/0082833 | A1 | 4/2004 | Adler et al. |
| 2006/0183976 | A1 | 8/2006 | Adler et al. |
| 2009/0054764 | A1 | 2/2009 | Adler et al. |
| 2010/0245550 | A1 | 9/2010 | Ishihara |
| 2012/0215066 | A1* | 8/2012 | Akiyama et al. ............. 600/109 |
| 2013/0271587 | A1* | 10/2013 | Tsuyuki .......................... 348/71 |
| 2014/0176692 | A1* | 6/2014 | Tsuyuki et al. ................ 348/68 |

FOREIGN PATENT DOCUMENTS

| | | |
|---|---|---|
| JP | 2003-078802 | 3/2003 |
| JP | 2003-290134 | 10/2003 |
| JP | 2003-529432 | 10/2003 |
| JP | 2004-313523 | 11/2004 |
| JP | 2004-337379 | 12/2004 |
| JP | 2010-004090 | 1/2010 |
| JP | 2010-220890 | 10/2010 |
| WO | 2013/046902 | 4/2013 |
| WO | 2013/061819 | 5/2013 |

* cited by examiner

ENDOSCOPE

CROSS-REFERENCE TO RELATED APPLICATIONS

This is a continuation of International Application PCT/JP2013/070316, with an international filing date of Jul. 26, 2013, which is hereby incorporated by reference herein in its entirety. This application claims the benefit of Japanese Patent Application No. 2012-190436, the contents of which are incorporated herein by reference.

TECHNICAL FIELD

The present invention relates to an endoscope.

BACKGROUND ART

In equipment provided with an imaging device, including endoscopes, it is generally known that increasing the number of pixels in an imaging device decreases a depth of field thereof. That is, in an imaging device, when the pixel pitch (vertical/horizontal dimension of one pixel) is decreased in order to increase the number of pixels, because the permissible circle of confusion is also decreased in association with this, the depth of field of an imaging apparatus is decreased. In order to increase the depth of field, for example, with the disclosure in Patent Literature 1, a subject image is split into two images that are focused differently by an optical-path splitting part, these images are separately formed in different imaging devices, and an image whose depth of field is increased is acquired by combining the two images.

On the other hand, to maintain the depth of field, it is conceivable to increase the f-number of an optical system. However, there is a problem in that the image quality is deteriorated due to an increase in noise, and the resolving power is decreased due to an increased influence of diffraction. As a technique for enhancing the resolving power, for example, Patent Literature 2 discloses a technique in which two subject images that are split by an optical-path splitting element and that are focused differently are formed in one imaging device, and a combined image in which the resolving power is enhanced is acquired by applying addition processing to the two images.

CITATION LIST

Patent Literature

{PTL 1} Japanese Unexamined Patent Application, Publication No. 2003-078802
{PTL 2} Japanese Unexamined Patent Application, Publication No. 2004-313523

SUMMARY OF INVENTION

Technical Problem

With the technique in Patent Literature 1 described above, because a plurality of imaging devices are provided in order to form subject images that are focused differently, the size of the imaging apparatus is increased, and the manufacturing cost thereof is increased. In addition, with the technique in Patent Literature 2, although it is possible to realize an increased dynamic range and enhanced resolving power, because the focus difference between the two subject images is too large, a region in which a good focus cannot be achieved is created between the individual depths of field, or that the depth of field cannot be increased because the overlap between the individual depths is too large.

The present invention provides an endoscope with which an image whose depth of field is increased can be acquired without increasing the size of the apparatus.

Solution to Problem

An aspect of the present invention provides an endoscope including an objective optical system that is provided at a distal end of an inserted portion and that acquires a subject image; an optical-path splitting part for splitting the subject image into two optical images that are focused differently; an imaging device that acquires two images by capturing the two optical images, which are focused differently, at the same time in a state in which the two optical images are arranged on an imaging surface; and a blocking part for cutting out at least abutting portions of the two optical images that are arranged on the imaging device, wherein the following conditional expression is satisfied:

$$A+B>C+D \tag{1},$$

where A is half the maximum length of the light-receiving regions for the optical images at the imaging surface; assuming that TW is an entry angle (in the case in which the imaging surface in the air) at the imaging surface when A is at the maximum image height and d is an optical-path-length difference (air-equivalent length) between the two optical images, B is given by $$B = d \times \tan TW;$$

C is half the length of the light-receiving regions in a direction in which the individual optical images, which are formed on the imaging surface, are arranged; and D is a size of a space between the two light-receiving regions.

With this aspect, light that has entered the objective optical system from the distal end of the inserted portion is split into the two optical paths by the optical-path splitting part, the two optical images that are arranged on the imaging surface of the imaging device and that are focused differently are captured at the same time by the imaging device, and thus, the two images that are focused differently are acquired. By combining the two images acquired in this way, it is possible to enhance the depth of field.

In this case, because at least the abutting portions of the two optical images that are arranged on the imaging device are cut out by the blocking part, the two beams that form the two optical images can be brought close to each other. In particular, by providing the blocking part, the optical images do not overlap even if the beams are brought close to each other to the positions that satisfy Conditional Expression (1), which would cause the two optical images to overlap with each other, and thus, an image whose depth of field is increased can be acquired, while reducing the size of the imaging device.

With the above-described aspect, the optical-path splitting part may be provided with a polarization splitting surface that is disposed at an angle of 45° with respect to an incidence optical axis, a mirror that deflects light that has been deflected at the polarization splitting surface so as to be folded by 180°; a λ/4 plate that is disposed between the mirror and the polarization splitting surface; and a deflection surface that deflects by 90° light that has passed through the polarization splitting surface. In addition, light that has entered thereinto may be propagated along two optical paths having different lengths and may be made to exit therefrom as two substantially parallel beams.

By employing such a configuration, the light polarized at the polarization splitting surface is made to enter the imaging device after being deflected twice at the polarization splitting surface and the mirror. On the other hand, the light that has passed through the polarization splitting surface is made to enter the imaging device by being deflected just once at the deflection surface. Therefore, the optical images formed by the two beams that have passed through two optical paths split by the optical-path splitting part are symmetrically reversed with reference to an intermediate line between the two optical images because the number of deflections differs by one.

With the above-described aspect, the blocking part may be provided with a flare diaphragm that blocks, of a beam that enters the polarization splitting surface of the optical-path splitting part, at least a portion of the beam on a mirror side.

By employing such a configuration, the beam, a portion of which is blocked by the flare diaphragm, is split into the two optical paths and made to enter the imaging device. By blocking the portion of the beam on the mirror side, because abutting portions of the two optical images that are formed in mirror symmetry are cut out, the two optical images can be brought close to each other in a simple manner, and the size of the imaging device can easily be reduced.

With the above-described aspect, the flare diaphragm may have a circular-arc opening edge that protrudes inward.

By employing such a configuration, even if the flare diaphragm is disposed at a position that is displaced from an image-formation point in the optical-axis direction, bulging of the optical images due to spread of the beams can be suppressed, the abutting portions between the optical images can be formed in straight lines, and thus, the size of the imaging device can be reduced by bringing the optical images sufficiently close to each other.

With the above-described aspect, the blocking part may be a blocking member that is disposed between the two beams that are made to exit from the optical-path splitting part and that is formed of a material that reflects or absorbs light.

By employing such a configuration, abutting portions of the two beams that are made to exit from the optical-path splitting part are reflected or absorbed by the blocking member, and thus, the two beams can be prevented from overlapping on the imaging surface of the imaging device.

The above-described aspect may satisfy the following conditional expressions $$0° \leq TW \leq 20°$$

$$0.001 \text{ mm} \leq d \leq 0.1 \text{ mm}$$

With the above-described aspect, the objective optical system may be formed of, sequentially from an object side, a negative lens group and a positive lens group, and the blocking member may be disposed between the negative lens group and the positive lens group.

Advantageous Effects of Invention

The present invention affords an advantage in that an image whose depth of field is more effectively increased can be acquired without increasing the size of an apparatus.

DESCRIPTION OF EMBODIMENT

An endoscope according to an embodiment of the present invention will be described below with reference to the drawings.

Figure 1:
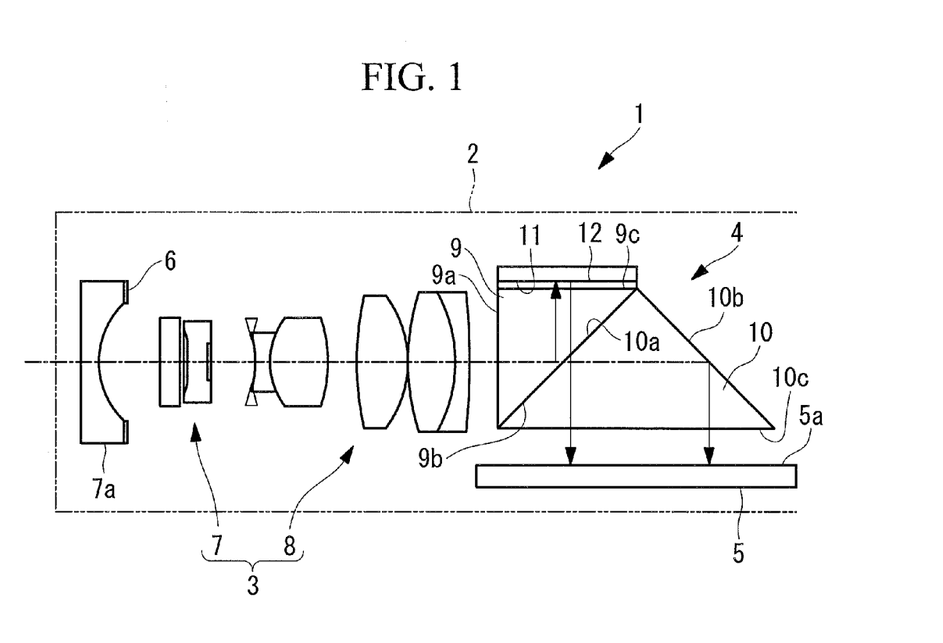
FIG. 1 is a diagram showing the arrangement of optical components at the distal end of an inserted portion of an endoscope according to an embodiment of the present invention.

As shown in FIG. 1, an endoscope 1 according to this embodiment is provided with an objective optical system 3 that is disposed in an inserted portion 2 which is inserted into an examination subject, an optical-path splitting part 4 for splitting light collected by the objective optical system 3 into two optical paths, an imaging device 5 that acquires two images at the same time by capturing the light split by the optical-path splitting part 4, and a flare diaphragm (a blocking part) 6 that partially cuts out the two optical images formed on the imaging device 5.

As shown in FIG. 1, the objective optical system 3 is provided with, sequentially from the object side, a negative lens group 7 and a positive lens group 8. Light that is coming from a wide viewing-field area and that is refracted by the negative lens group 7 is focused by the positive lens group 8 and is made to exit toward the optical-path splitting part 4 provided at the subsequent stage.

The optical-path splitting part 4 is formed by combining two, namely, large and small, triangular prisms 9 and 10, a mirror 11, and a λ/4 plate 12.

The first prism 9 is provided with a first surface 9a that is perpendicular to the optical axis of the objective optical system 3, a second surface 9b that forms an angle of 45° with respect to the optical axis, and a third surface 9c that is parallel to the optical axis. The second prism 10 is provided with a first surface 10a and a second surface 10b that form angles of 45° with respect to the optical axis of the objective optical system 3 and a third surface 10c that is parallel to the optical axis. The first surface 10a and the second surface 10b of the second prism 10 are perpendicular to each other.

The first surface 9a of the first prism 9 constitutes an entrance surface at which a beam coming from the objective optical system 3 enters.

Polarization splitting surfaces are constituted by placing a polarization splitting film (not shown) between the second surface 9b of the first prism 9 and the first surface 10a of the second prism 10, in close contact therewith without a space.

The second surface 10b of the second prism 10 constitutes a deflection surface that deflects by 90° light that has advanced inside the second prism 10 in the optical-axis direction.

The mirror 11 is disposed so as to sandwich the λ/4 plate 12 together with the third surface 9c of the first prism 9.

By doing so, the beam exiting from the objective optical system 3 is made to enter the first prism 9 from the first surface 9a of the first prism 9 and is subsequently split into a P polarized component (transmitted light) and an S polarized component (reflected light) at the polarization splitting surfaces (9b and 10a) where the polarization splitting film is disposed.

The reflected light from the polarization splitting surfaces is made to pass through the λ/4 plate 12 from the third surface 9c of the first prism 9, is deflected by the mirror 11 so as to be folded by 180°, is made to pass through the λ/4 plate 12 again, which rotates the polarization direction thereof by 90°, is subsequently made to pass through the polarization splitting film, and is made to exit from the third surface 10c of the second prism 10 to the exterior.

On the other hand, the transmitted light from the polarization splitting surfaces advances inside the second prism 10, is deflected by 90° at the second surface 10b of the second prism 10, and is made to exit from the third surface 10c of the second prism 10 to the exterior.

Until exiting from the third surface 10c of the second prism 10 after entering the first prism 9 from the first surface 9a of the first prism 9, the optical path lengths of the light that advances in the two split optical paths have a slight difference therebetween, for example, an optical-path-length difference d of several micrometers to several tens of micrometers.

Accordingly, as described later, optical images due to the two beams that are made to enter the imaging device 5, which is disposed facing the third surface 10c of the second prism 10, have slightly different focusing positions.

The imaging device 5 has an imaging surface 5a that is made to face the third surface 10c of the second prism 10 so as to be parallel thereto and have a space with respect thereto, and the two beams exiting from the third surface 10c of the second prism 10 are made to enter the imaging device 5 at the same time.

Figure 2:
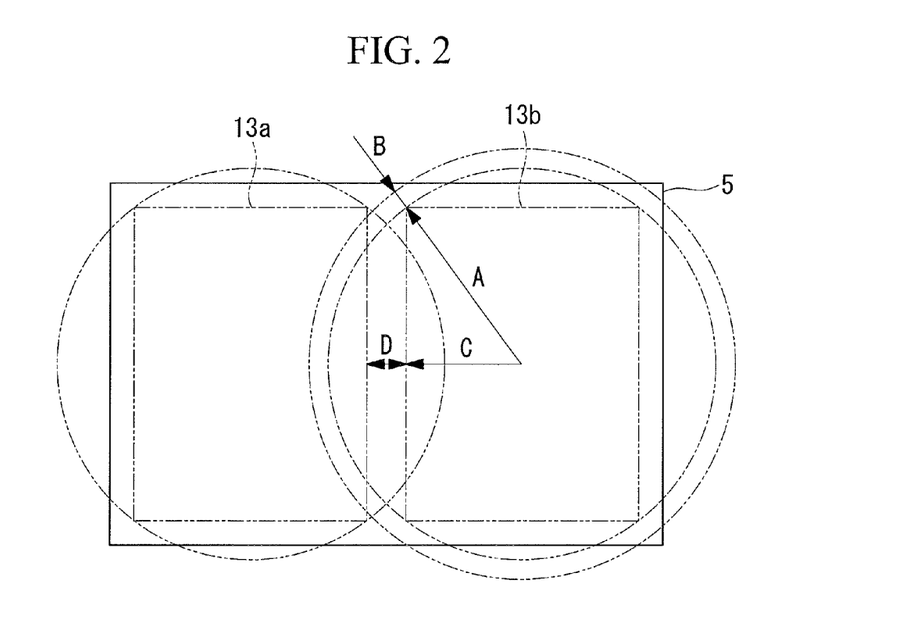
FIG. 2 is a diagram showing light-receiving regions on an imaging device of the endoscope in FIG. 1.

Specifically, as shown in FIG. 2, in order to capture the two optical images that have different focusing positions at the same time, the imaging device 5 is provided with two rectangular light-receiving regions (effective pixel regions) 13a and 13b within the entire pixel region of the imaging device 5.

In order to capture the two optical images, the light-receiving regions 13a and 13b are disposed so as to substantially coincide with the image-formation surfaces for these optical images. Also, in the imaging device 5, the light-receiving region 13a has its focusing position shifted (displaced) toward the near-point side relative to the light-receiving region 13b, and the light-receiving region 13b has its focusing position shifted toward the far-point side relative to the light-receiving region 13a. By doing so, the two optical images that are focused differently are formed on the imaging surface 5a of the imaging device 5.

The focusing positions of the light-receiving regions 13a and 13b may be relatively displaced by making the first prism 9 and the second prism 10 differ from each other in terms of refractive index, thus changing the lengths of optical paths leading to the imaging device 5.

Figure 3:
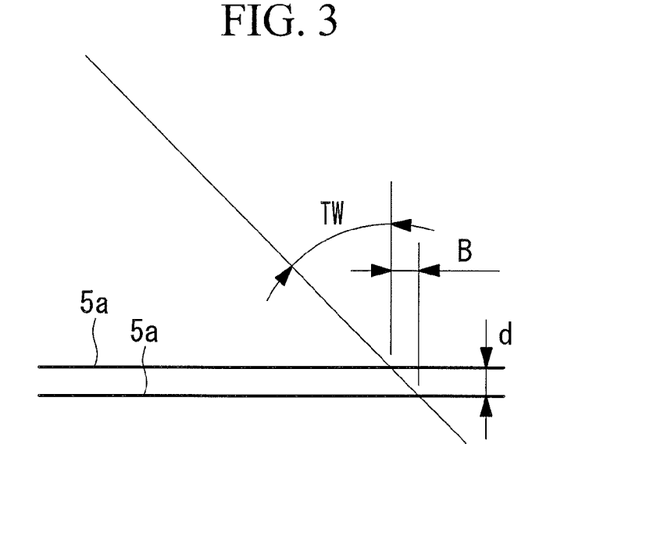
FIG. 3 is a diagram for explaining the spread of optical images due to an optical-path-length difference between two optical paths of the endoscope in FIG. 1.

In addition, with the endoscope 1 according to this embodiment, the two rectangular light-receiving regions 13a and 13b are arranged on the imaging device 5 so as to satisfy the following conditional expression:

$$A+B>C+D \quad (1),$$

where, in FIGS. 2 and 3, A is half the maximum length of the light-receiving region 13a or the light-receiving region 13b (maximum image height of an optical image that can be displayed on a monitor); assuming that TW is an entry angle (in the case in which the imaging surface 5a in the air) at the imaging surface 5a of the imaging device 5 when A is at the maximum image height and d is an optical-path-length difference (air-equivalent lengths) between the two optical images, B is given by $$B=d\times\tan TW;$$

C is half the length of the light-receiving regions in the direction in which the individual optical images, which are formed on the imaging surface 5a of the imaging device 5, are arranged; and D is the size of a space between the two light-receiving regions.

The above-described light-receiving regions indicate the regions in which optical images in these regions can be displayed on a monitor. When performing image processing such as positional correction of the two images and so forth, these regions may be defined as regions including margins needed for image processing. In addition, the shape of light-receiving regions is not limited to a rectangle, and it may be an octagon or a circle. Half the maximum length including the centers of the light-receiving regions may be defined as A. For example, in the case of circles, the radii of the circle correspond to A and C.

Figure 4:
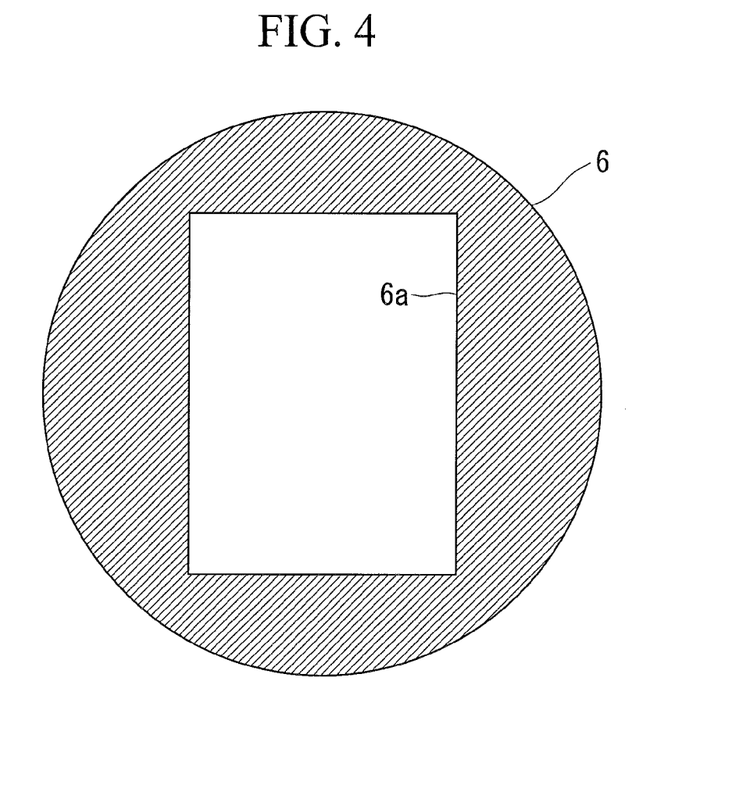
FIG. 4 is a diagram showing an example of a flare diaphragm of the endoscope in FIG. 1.

As shown in FIG. 4, the flare diaphragm 6 has a rectangular opening 6a and blocks and cuts out peripheral portions of the beam that has entered the objective optical system 3.

The operation of the thus-configured endoscope 1 according to this embodiment will be described below.

To observe a portion to be examined in an examination subject by using the endoscope 1 according to this embodiment, the distal-end surface of the inserted portion 2 is inserted into the examination subject so as to be disposed facing the portion to be examined. Then, illumination light is radiated from a light source (not shown), and reflected light returning from the examination subject or fluorescence generated at the examination subject is collected by the objective optical system 3.

After the cross-sectional shape of a beam refracted at a distal-end lens 7a of the negative lens group 7 of the objective optical system 3 is reshaped by passing through the flare diaphragm 6, the beam is made to enter from the first surface 9a of the first prism 9 while being focused by the positive lens group 8.

The beam that has entered the first prism 9 is split into the reflected light and the transmitted light at the polarization splitting surfaces 9b and 10a.

The light reflected from the polarization splitting surfaces 9b and 10a and transmitted through the third surface 9c of the first prism 9, the λ/4 plate 12, the mirror 11, the λ/4 plate 12, and the third surface 9c of the first prism 9 is subsequently made to exit from the third surface 10c of the second prism 10 by passing through the polarization splitting surfaces 9b and 10a, and forms an image on the imaging surface 5a of the imaging device 5 disposed facing the third surface 10c.

On the other hand, the transmitted light from the polarization splitting surfaces 9b and 10a is deflected by 90° at the second surface 10b of the second prism 10, is made to exit from the third surface 10c, and forms an image on the imaging surface 5a of the imaging device 5.

Because the optical path lengths of the light that reaches the imaging surface 5a of the same imaging device 5 by passing through the two optical paths have the optical-path-length difference d therebetween, two optical images that are focused differently are formed on the two light-receiving regions 13a and 13b of the imaging device 5. Therefore, by combining the acquired two images, an image with a large depth of field can be obtained.

In this case, in this embodiment, because the beam is reshaped into a beam having a substantially rectangular cross section when peripheral light portions of the beam are blocked by the flare diaphragm 6 provided at the subsequent stage of the distal-end lens 7a of the negative lens group 7, there is an advantage in that the two optical images are not overlapped and a clear image can be acquired, even if the light-receiving regions 13a and 13b are brought close to each other on the imaging surface 5a of the imaging device 5 so as to satisfy Conditional Expression (1).

Also, by bringing the two light-receiving regions 13a and 13b sufficiently close to each other, the size of the imaging device 5 can be reduced, and the diameter of the inserted portion 2 that accommodates the imaging device 5 can be reduced.

In addition, by cutting out the peripheral light portions of the beam, there is an advantage in that the ray height of the beam that enters the first prism 9 can be decreased, thus reducing flare that is generated inside the first prism 9 and the second prism 10.

In this embodiment, as the flare diaphragm 6, although one having the rectangular opening 6a has been described as an example, as shown in FIG. 4, in the case in which the position at which the flare diaphragm 6 is installed is greatly separated from the subject position in the optical-axis direction, rectangular optical images are not formed at the imaging surface, and the optical images will have a shape in which individual sides of the rectangle bulge outward.

Figure 5:
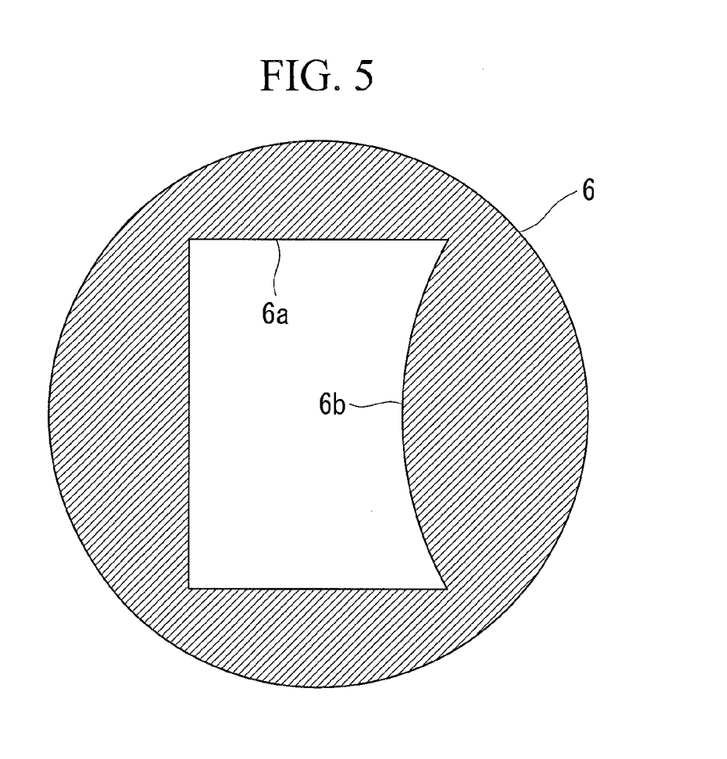
FIG. 5 is a diagram showing a modification of the flare diaphragm in FIG. 4.

In this case, for example, as shown in FIG. 5, it is preferable that an opening edge 6b of at least one side of the opening 6a of the flare diaphragm 6 be formed as a circular arc that protrudes inward. This opening edge 6b is disposed at a position of the flare diaphragm 6 in the objective optical system 3 in FIG. 1 and is also disposed so that the opening edge 6b is opposite the mirror 11 with respect to the optical axis.

Figure 6:
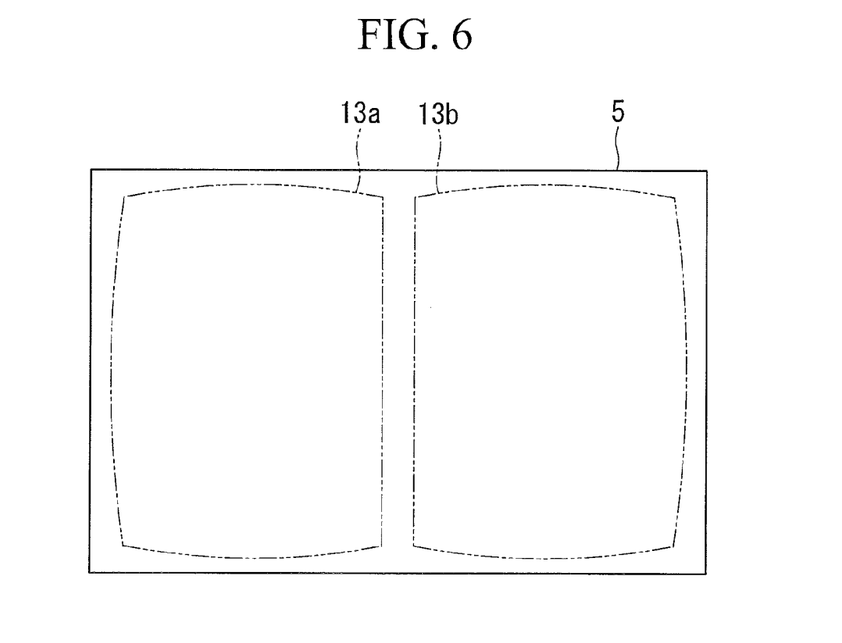
FIG. 6 is a diagram showing optical images on the imaging device in the case in which the flare diaphragm in FIG. 5 is employed.

By employing such a configuration, the beams from portions where peripheral light portions on the mirror 11 side are greatly cut out are disposed on the abutting sides of the two optical images formed on the imaging surface 5a of the imaging device 5. As a result, as shown in FIG. 6, portions that correspond to the opening edge 6b are maintained as straight lines even if the optical images that are formed on the imaging surface 5a bulge outward, and therefore, the two optical images can be brought sufficiently close to each other, and the size of the imaging device 5 can be reduced.

Figure 7:
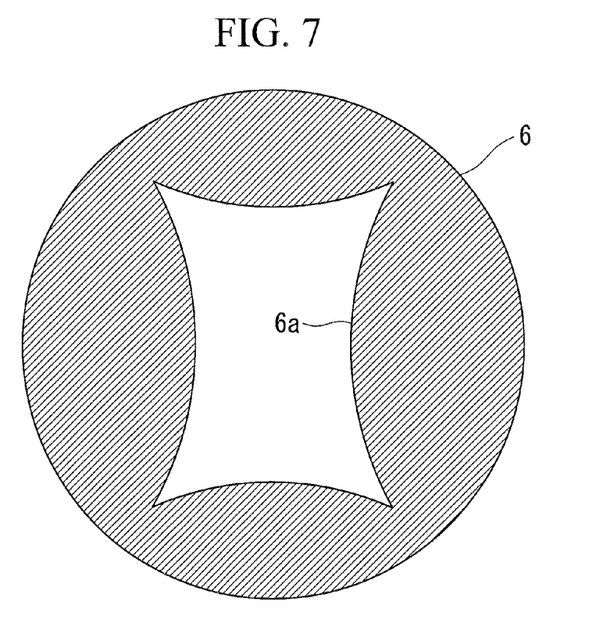
FIG. 7 is a diagram showing another modification of the flare diaphragm in FIG. 4.

In addition, although only the opening edge 6b on one side is assumed to take the shape that protrudes inward, the rectangular optical images may be formed on the imaging device 5 by employing an opening 6a having a shape in which opening edges protrude inward at two or more sides, for example, at all four sides, as shown in FIG. 7.

Figure 8:
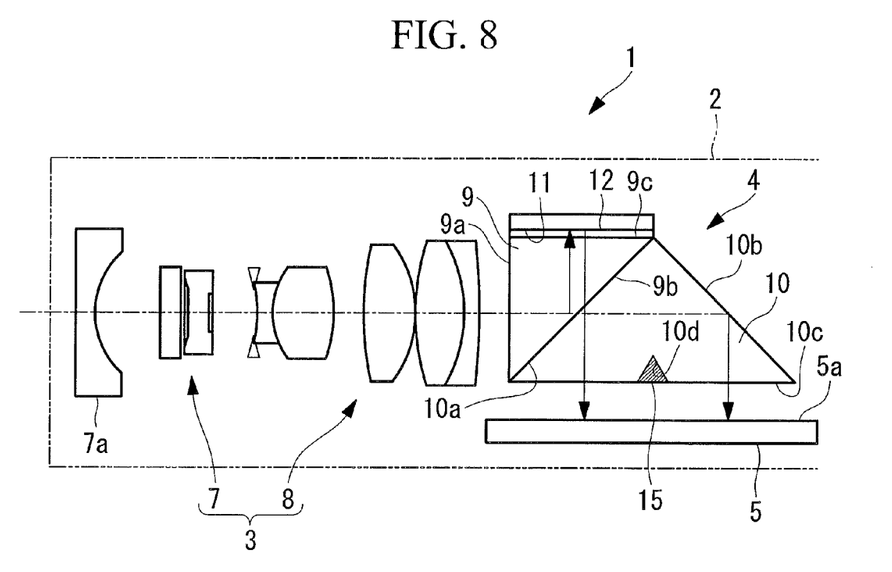
FIG. 8 is a diagram showing a modification of the endoscope in FIG. 1.
Figure 9:
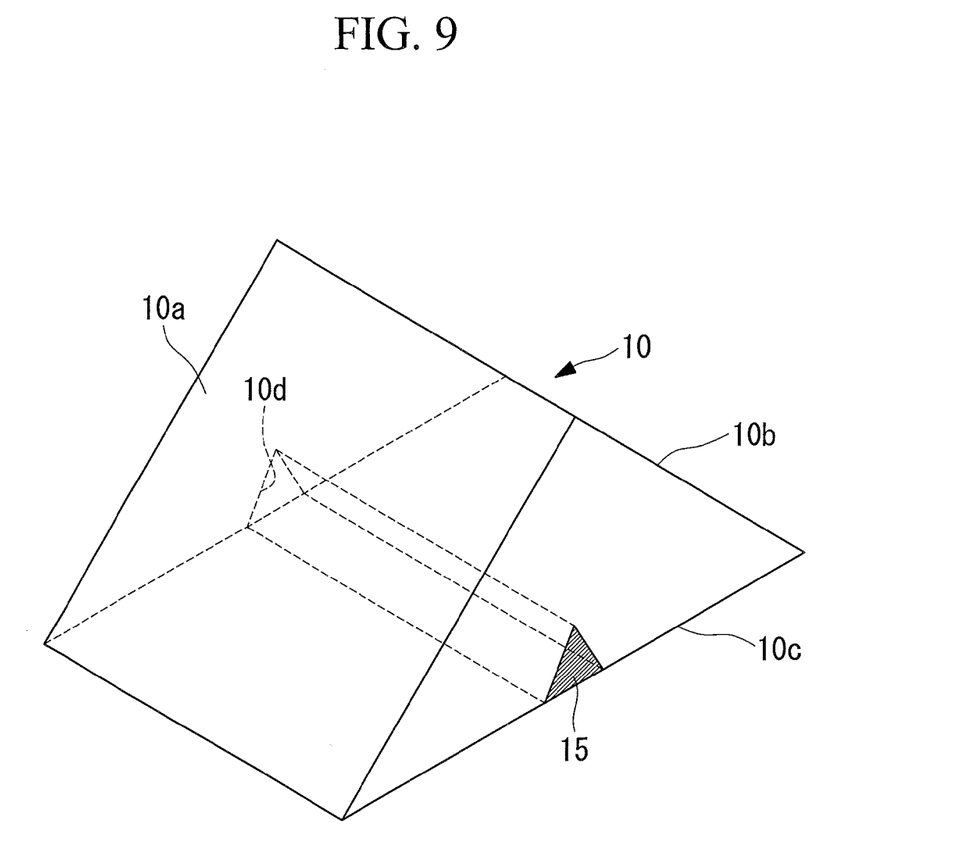
FIG. 9 is a perspective view showing a light-blocking member of the endoscope in FIG. 8.

In this embodiment, although an example in which the flare diaphragm 6 is employed to prevent the two optical images from overlapping has been described, there is no limitation to the position at which the flare diaphragm 6 is disposed, and it may be disposed at the first surface 9a of the first prism 9. Alternatively, as shown in FIGS. 8 and 9, a blocking member 15 may be disposed at a position that separates the two beams exiting from the third surface 10c of the second prism 10.

The blocking member 15 is formed in a triangular columnar shape having a black color that absorbs light, and is mated with and attached to a triangular groove 10d formed in the third surface 10c of the second prism 10. Alternatively, the blocking member 15 may be formed by filling the triangular groove 10d with hardening black paint.

In addition, blocking member 15 is not limited to the triangular columnar shape, and it may be formed in a columnar shape having any other sectional shape.

REFERENCE SIGNS LIST 1 endoscope
2 inserted portion
3 objective optical system
4 optical-path splitting part
5 imaging device
5a imaging surface
6 flare diaphragm (blocking part)
6b opening edge
7 negative lens group
8 positive lens group
9b second surface (polarization splitting surface)
10a first surface (polarization splitting surface)
10b second surface (deflection surface)
11 mirror
12 $\lambda/4$ plate
15 blocking member (blocking part)

The invention claimed is:

1. An endoscope comprising:
an objective optical system that is provided at a distal end of an inserted portion and that acquires a subject image;
an optical-path splitting part for splitting the subject image into two optical images that are focused differently;
an imaging device that acquires two images by capturing the two optical images, which are focused differently, at the same time in a state in which the two optical images are arranged on an imaging surface; and
a blocking part for cutting out at least abutting portions of the two optical images that are arranged on the imaging device,
wherein the following conditional expression is satisfied:

$$A+B>C+D,$$

where A is half the maximum length of light-receiving regions for the optical images at the imaging surface;
assuming that TW is an entry angle (in the case in which the imaging surface is in air) at the imaging surface when A is at the maximum image height and d is an optical-path-length difference (air-equivalent length) between the two optical images, B is given by $$B=d\times\tan TW;$$

C is half the length of the light-receiving regions in a direction in which the individual optical images, which are formed on the imaging surface, are arranged; and
D is a size of a space between the two light-receiving regions.

2. The endoscope according to claim 1, wherein the optical-path splitting part is provided with a polarization splitting surface that is disposed at an angle of 45° with respect to an incidence optical axis, a mirror that deflects light that has been deflected at the polarization splitting surface so as to be folded by 180°; a $\lambda/4$ plate that is disposed between the mirror and the polarization splitting surface; and a deflection surface that deflects by 90° light that has passed through the polarization splitting surface, and
wherein light that has entered thereinto is propagated along two optical paths having different lengths and is made to exit therefrom as two substantially parallel beams.

3. The endoscope according to claim 2, wherein the blocking part is provided with a flare diaphragm that blocks, of a beam that enters the polarization splitting surface of the optical-path splitting part, at least a portion of the beam on a mirror side.

4. The endoscope according to claim 3, wherein the flare diaphragm has a circular-arc opening edge that protrudes inward.

5. The endoscope according to claim 2, wherein the blocking part is a blocking member that is disposed between the two beams that are made to exit from the optical-path splitting part and that is formed of a material that reflects or absorbs light.

6. The endoscope according to claim 1, wherein the following conditional expressions are satisfied:

$0° \leq TW \leq 20°$; and $0.001 \text{ mm} \leq d \leq 0.1 \text{ mm}$.

7. The endoscope according to claim 3, wherein the objective optical system is formed of, sequentially from an object side, a negative lens group and a positive lens group, and the blocking member is disposed between the negative lens group and the positive lens group.

* * * * *